US008652807B2

(12) United States Patent
Charneau et al.

(10) Patent No.: US 8,652,807 B2
(45) Date of Patent: *Feb. 18, 2014

(54) LENTIVIRAL VECTORS FOR THE PREPARATION OF IMMUNOTHERAPEUTICAL COMPOSITIONS

(71) Applicants: Institut Pasteur, Paris (FR); Institut National de la Santé et de la Recherche Médicale, Paris (FR); Centre National de la Recherche Scientifique, Paris (FR)

(72) Inventors: Pierre Charneau, Paris (FR); Huseyin Firat, Paris (FR); Véronique Zennou, Paris (FR)

(73) Assignees: Institut Pasteur, Paris (FR); Institut National de la Santé et de la Recherche Médicale, Paris (FR); Centre National de la Recherche Scientifique, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/711,898

(22) Filed: Dec. 12, 2012

(65) Prior Publication Data

US 2013/0157357 A1 Jun. 20, 2013

Related U.S. Application Data

(60) Continuation of application No. 13/104,380, filed on May 10, 2011, now Pat. No. 8,349,606, which is a division of application No. 10/313,038, filed on Dec. 6, 2002, now Pat. No. 7,968,332, which is a continuation of application No. 10/118,915, filed on Apr. 10, 2002, now abandoned, which is a continuation of application No. PCT/EP00/10419, filed on Oct. 10, 2000.

(30) Foreign Application Priority Data

Oct. 11, 1999 (EP) .................. 99402492.5

(51) Int. Cl.
*C12N 15/00* (2006.01)
*C12N 15/09* (2006.01)
*C12N 15/63* (2006.01)

(52) U.S. Cl.
USPC ..... 435/70.3; 435/69.1; 435/701.1; 435/70.4; 435/455; 435/466; 435/235.1

(58) Field of Classification Search
None
See application file for complete search history.

(56) References Cited

U.S. PATENT DOCUMENTS

| | | | |
|---|---|---|---|
| 6,682,907 B1 | 1/2004 | Charneau et al. | |
| 7,968,332 B2 | 6/2011 | Charneau et al. | |
| 7,981,671 B2 | 7/2011 | Charneau et al. | |
| 8,093,042 B2 | 1/2012 | Charneau et al. | |
| 2003/0072938 A1 | 4/2003 | Kappes et al. | |
| 2003/0194392 A1 | 10/2003 | Charneau et al. | |
| 2004/0081636 A1 | 4/2004 | Charneau et al. | |
| 2006/0040347 A1 | 2/2006 | Charneau et al. | |
| 2007/0087354 A1 | 4/2007 | Charneau et al. | |
| 2007/0224679 A1 | 9/2007 | Charneau et al. | |
| 2010/0028382 A1 | 2/2010 | Charneau et al. | |
| 2010/0221820 A1 | 9/2010 | Charneau et al. | |
| 2011/0250650 A1 | 10/2011 | Charneau et al. | |
| 2012/0095083 A1 | 4/2012 | Charneau et al. | |
| 2012/0122204 A1 | 5/2012 | Charneau et al. | |
| 2012/0122963 A1 | 5/2012 | Charneau et al. | |
| 2012/0252113 A1 | 10/2012 | Charneau et al. | |
| 2012/0252114 A1 | 10/2012 | Charneau et al. | |

FOREIGN PATENT DOCUMENTS

| | | |
|---|---|---|
| EP | 0 611 822 A2 | 8/1994 |
| WO | WO 97/12622 A1 | 4/1997 |
| WO | WO 97/32983 A1 | 9/1997 |
| WO | WO 98/39463 A2 | 9/1998 |
| WO | WO 98/46083 A1 | 10/1998 |
| WO | WO/99/55892 A1 | 11/1999 |
| WO | WO 00/31280 A2 | 6/2000 |

OTHER PUBLICATIONS

Parolin, C., Analysis in Human Immunodeficiency Virus Type 1 Vectors of cis-Acting Sequences That Affect Gene Transfer into Human Lymphocytes. Journal of Virology Jun. 1994, vol. 68, No. 6, p. 3888-3895.

Zufferey et al., Multiply attenuated lentiviral vector achieves efficient gene delivery in vivo; Nature Biotechnology, vol. 15, (1997) 871-875.

Charneau et al., HIV-1 Reverse Transcription, A termination step at the center of the genome; J. Mol. Biol. (1994) 241, 651-662.

Charneau et al., A single-stranded gap in human immunodeficiency virus unintegrated linear DNA defined by a central polypurine tract; J. Virol. (1991) 65, 2415-2421.

Charneau et al., A second origin of DNA plus-strand synthesis is required for optimal human immunodeficiency virus replication; J. Virol. (1992) 66, 2814-2820.

Erlwein et al., Sequences in pol are required for transfer of human foamy virus-based vectors; J. Virol. (1998) 72, 5510-5516.

Naldini et al., Efficient transfer, integration, and sustained long-term expression of the transgene in adult rat brains injected with a lentiviral vector; Proc. Natl. Acad. Sci. USA, (1996) vol. 93, 11382-11388.

(Continued)

*Primary Examiner* — Louise Humphrey
(74) *Attorney, Agent, or Firm* — Law Office of Salvatore Arrigo and Scott Lee, LLP

(57) ABSTRACT

The invention relates to an immunogenic composition comprising a recombinant vector characterized in that it comprises a polynucleotide comprising the cis-acting central initiation region (cPPT) and the cis-acting termination region (CTS), these regions being of retroviral or retroviral-like origin, said vector comprising in addition a defined nucleotide sequence (transgene or sequence of interest) and regulatory signals of retrotranscription, expression and encapsidation of retroviral or retroviral-like origin, wherein the composition is capable of inducing or of stimulating a cell-mediated response for instance a CTL (Cytotoxic T Lymphocytes) response or a CD4 response, against one or several epitopes encoded by the transgene sequence present in the vector.

25 Claims, 11 Drawing Sheets

(56) References Cited

OTHER PUBLICATIONS

Naldini et al., In vivo gene delivery and stable transduction of nondividing cells by a lentiviral vector; Science, vol. 272, (1996) 263-267.

Poznansky et al., Gene transfer into human lymphocytes by a defective human immunodeficiency virus type 1 vector; J. Virol. (1991) 65, 532-536.

Stetor et al., Characterization of (+) strand initiation and termination sequences located at the center of the equine infectious anemia virus genome; Biochem. (1999) vol. 38, 3656-3667.

Kim et al.; Temporal aspects of DNA and RNA synthesis during human immunodeficiency virus infection: Evidence for differential gene expression; J. Virol. (1989) 63, 3708-3713.

European Patent Office, International Search Report, PCT/EP00/10419, Feb. 5, 2001.

Rizvi et al., Propagation of SIV vectors by genetic complementation with a heterologous env gene, AIDS Research and Human Retroviruses, vol. 8, No. 1, pp. 89-95 (1992).

Giovannangeli et al., Accessibility of nuclear DNA to triplex-forming oligonucleotides: The integrated HIV-1 provirus as a target. Proceedings National Academy of Science, U.S.A., Jan. 1997, vol. 94, pp. 79-84.

Batra et al., Transduction of Non-Small Cell Lung Cancer Cells by Adenoviral and Retroviral Vectors, Am. J. Respir. Cell Mol. Biol., (1998) 18:402-410.

Blomer, U., et al., Abstract In-vitro and In-vivo Study of Gene Transfer with a New HIV Derived Vector, Zentralbl Neurochir Supplement (1996).

Johnson et al., Effect of Host Modification and Age on Airway Epithelial Gene Transfer Mediated by a Murine Leukemia Virus-Derived Vector, Journal of Virology, (1998) 72(11):8861-8872.

Matukonis et al, "Development of Second- and Third-Generation Bovine Immunodeficiency Virus-Based Gene Transfer Systems," Human Gene Therapy (2002) 13:1293-1303.

Molina et al.,"Mapping of Bovine Immunodeficiency Virus Packaging Signal and RRE and Incorporation into a Minimal Gene Transfer Vector," Virology (2002) 304:10-23.

Negre, D., ETA/.,"Characterization of Novel Safe Lentiviral Vectors Derived from Simian Immunodeficiency Virus (SIV mac251) that Efficiently Transduce Mature Human Dendritic Cells," Gene Therapy (2000) 7:1613-1623.

Olsen, JC, "Gene transfer vectors derived from equine infectious anemia virus," Gene Therapy (1998) 5:1481-1487.

Poeschla et al. "Efficient transduction of nondividing human cells by feline immunodeficiency virus lentiviral vectors," Nature Medicine (1998) 4(3) 354-357.

Poeschla et al. "Identification of a Human Immunodeficiency Virus Type 2 (HIV-2) Encapsidation Determinant and Transduction of Nondividing Human Cells by HIV-2-Based Lentivirus Vectors," Journal of Virology (1998) 72(8) 6527-6536.

Sirven, "The human immunodeficiency virus type-1 central DNA Flap is a crucial determinant for lentiviral vector nuclear import and gene transduction of human hematopoietic stem cells," Blood (2000) 92(13) 4103-4110.

Sallberg et al., Characterization of humoral and CD4+ cellular responses after genetic immunization with retroviral vectors expressing different forms of hepatitis B virus core and e antigens, J. Virology, vol. 71, No. 7, pp. 5295-5303 (1997).

Zennou et al., "HIV-1 Genome Nuclear Import Is Mediated by a Central DNA Flap", Cell, vol. 101, pp. 173-185 (2000).

Zennou et al., "The HIV-1 DNA flap stimulates HIV vector-mediated cell transduction in the brain", Nature Biotechnology, vol. 19, pp. 446-450 (2001).

Lavigne et al., DNA Curvature Controls Temperature of Plus Strand DNA Synthesis at the Center of HIV-1 Genome. Journal of Molecular Biology 1997, vol. 266, p. 507-524.

Figure 1: HIV1-derived central DNA positive recombinant vector encoding a melanoma polyepitope Melanoma polyepitopic sequence AAGIGILTVFLWGPRALVMLLAVLYCLLLDGTATLRLKTWGQYWQV
YMDGTMSQVITDQVPFSVYLEPGPVTAILTVILGVLVLPDVFIRCV Figure 2: CTL responses of HHD mice after immunization with the TRIP-mel-IRES-GFP vector Figure 3: GFP expression in human dendritic cells 5 days after their transduction by the central DNA triplex positive or negative HIV 1-derived vectors Figure 4: In vitro CTL responses using human dendritic cells

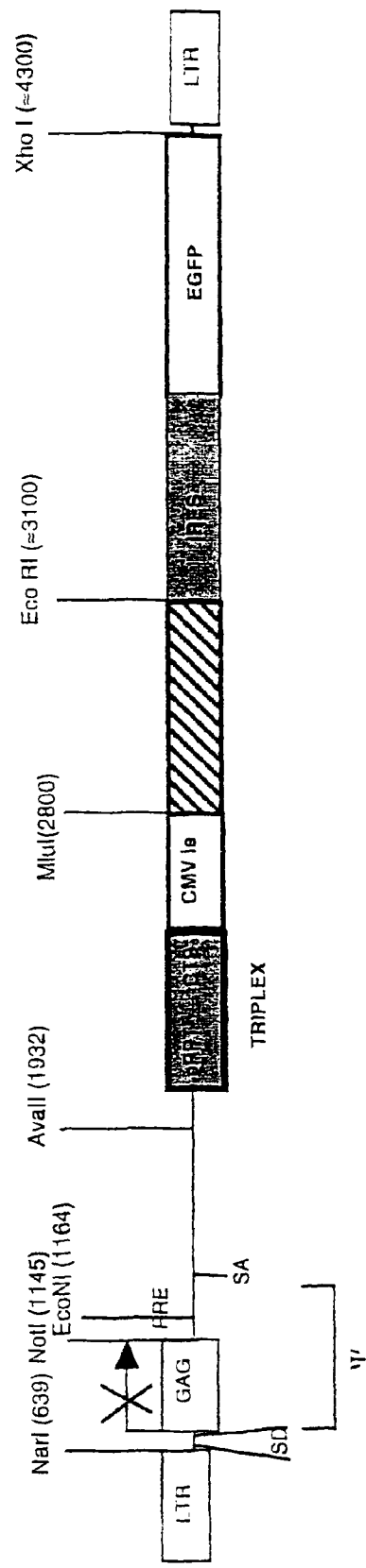
FIGURE 6
: HIV specific CTLs mono or polyepitopical sequences, the epitope of which I9V.(ILKE); RT 476-484)

Figure 9 : Evaluation of CTL responses in HHD mice after immunization with the TRIP-des-IRES-GFP vector encoding the DES gene of Mycobacterium tuberculosis

LENTIVIRAL VECTORS FOR THE PREPARATION OF IMMUNOTHERAPEUTICAL COMPOSITIONS

CROSS-REFERENCE TO RELATED APPLICATIONS

This application is a continuation of U.S. application Ser. No. 13/104,380, filed May 10, 2011, now U.S. Pat. No. 8,349,606, which is a divisional of U.S. application Ser. No. 10/313,038, filed Dec. 6, 2002, now U.S. Pat. No. 7,968,332, which is a continuation of U.S. application Ser. No. 10/118,915, filed Apr. 10, 2002, now abandoned, which is a continuation of International Application PCT/EP00/10419, filed Oct. 10, 2000, which claims the benefit of European Application EP 99402492.5, filed Oct. 11, 1999, all of which are incorporated by reference.

PARTIES TO JOINT RESEARCH AGREEMENT

The inventions claimed herein were made as a result of activities undertaken within the scope of a Joint Research Agreement between Assignees Institut Pasteur and Centre National de la Recherche Scientifique, entered into before Oct. 11, 1999.

BRIEF DESCRIPTION OF THE INVENTION

The present invention relates to the use of retroviral vectors, and especially lentiviral vectors for the preparation of compositions which are capable of inducing or contributing to the occurrence or improvement of an immunological reaction in vitro, and in a preferred embodiment in vivo, against epitopes which are encoded by nucleotide sequences present in the vectors.

The inventors have shown that vectors prepared in accordance with the present invention enable to obtain a cell-mediated immune response, especially a Cytotoxic T Lymphocytes (CTL) reaction against epitopes.

They have furthermore obtained data showing that this cell-mediated immune response can be a specific response, obtained against one or several epitopes encoded by the nucleotide sequence contained in the vectors.

Therefore, the invention provides means which could be used in treatment protocols against tumors and cancer and especially could be used in protocols for immunotherapy or vaccination therapy against tumors.

The invention also discloses means that could be used for the treatment or prophylaxis of infectious diseases, especially diseases associated with virus infection and for instance, with retrovirus infection.

The inventors have further obtained results showing that the cell-mediated immune response and especially the CTL response associated with the treatment by the compositions of the invention can be specific for the antigen of the tumor or of the virus or virus infected cells, and can also be restricted to specific molecules of the MHC (Major Histocompatibility Complex).

Particularly the invention relates to the use of the vectors in immunogenic compositions, in order to obtain a cell-mediated immune response restricted to Class I molecules of the MHC complex and for instance restricted to HLA-A2 or B7 molecules.

DETAILED DESCRIPTION OF THE INVENTION

Accordingly, the invention relates to an immunogenic composition comprising a recombinant vector which comprises a polynucleotide encompassing the cis-acting central initiation region (cPPT; central polypurine tract) and the cis-acting termination region (CTS; central termination sequence). During reverse transcription, cPPT and CTS sequences induce the formation of a three stranded DNA structure here referred as DNA triplex. The DNA triplex stimulates the nuclear import of vector DNA genomes, these regions being of retroviral or retroviral-like origin, said vector comprising in addition a defined nucleotide sequence (transgene or sequence of interest) and regulatory signals of retrotranscription, expression and encapsidation of retroviral or retroviral-like origin, wherein the composition is capable of inducing or of stimulating a CTL (Cytotoxic T Lymphocytes) or a CD4 response against one or several epitopes encoded by the transgene sequence present in the vector.

In a preferred embodiment of the invention, the cell-mediated immune response and especially the CTL response or the CD4 response against one or several epitopes is a memory CTL or a CD4 response.

It is emphasized that the presence, in the vector, of the cPPT and CTS regions enables the triplex DNA structure to be formed thereby influencing and especially improving the nuclear import of the genome of the vector in cells recombined with said vector.

This capacity of the immunogenic composition according to the invention to induce, improve or in general be associated with the occurrence of a memory CTL response, enables to propose the use of the immunogenic composition in protocols of anti-tumor therapy or antivirus or antipathogenic therapy, including when the immune response has to be induced on long lasting period of time or at least inducible when a response is sought at a period of time which can be long term induction of the response, after the administration of the immunogenic composition. In other words the immunogenic composition can be used for the preparation of therapeutic composition for the treatment of tumor diseases or infectious diseases, for instance by bacteria or viruses, by inducing or stimulating or participating to the occurrence of a cell-mediated immune response, especially a CTL response or a memory response.

It is emphasized that the immunogenic composition of the invention, as a consequence of the presence of the triplex structure in the sequence of the vector, resulting from the presence of the cPPT and CTS regions in the vector and in the vector particles, enables the stimulation of the nuclear import of the genome of the vector, in target cells. The induced epitopes in the vector can be self or non-self.

The present invention covers also the use of a nucleotidic sequence comprising the cPPT and CTS sequences of retroviral or synthetic origin for increasing the entry of nucleotidic or peptidic sequences in the nucleus of the target cells or recipient cells.

As an example, it is understood that the said triplex sequence comprises foreign sequences or self sequences with respect to the recipient cells.

Thus, the invention discloses a composition that could be used in therapeutic protocols that present analogies with vaccination protocols, for the treatment of tumors and especially as anti-cancer or anti-infectious diseases treatment.

It is of interest to note that in accordance with the present invention, this transgene or sequence of interest can be a sequence encoding one or several epitopes of one or several tumor cells, for instance epitopes that have been identified in potential target antigens for the induction of a cell-mediated immune response against the tumor.

Several epitopes forming a polyepitope, can be encoded by the transgene of the invention. In a particular embodiment, they can be derived from target antigens identified in the tumor, and can be chosen in such a way that when their coding sequence is combined to form the transgene, a cell-mediated immune response is obtained against all the epitopes or against most of them. The cell-mediated immune response can be assayed in vitro or in a preferred embodiment in vivo. Protocols enabling to carry out such assays are described in the Examples.

Target antigens have been identified in several types of tumors and in particular in melanomas or in carcinomas, including renal carcinomas, Bladder carcinomas, colon carcinomas, lung carcinomas, breast cancer, leukemia and lymphoma.

According to another aspect of the invention, the immunogenic composition can be used in order to obtain a cell-mediated immune response, in infectious diseases, including viral-associated infection, or infection linked to any kind of pathogen, including Mycobacteria, for instance, M tuberculosis.

In this case specific antigens capable of eliciting a cell-mediated immune response can be identified and their coding sequences inserted in the vector used in the immunogenic composition. As example the des gene of M tuberculosis can be used.

It is also added that in accordance with the present invention, the vectors which are used in the immunogenic compositions may express epitopes or present on proteins (including glycoproteins or other protein-derived compounds) identified as target antigens on tumor cells or on virus-infected cells.

In addition, it is noted that epitopes, polypeptides or proteins used to provide epitopes, can be modified, for instance by mutation, deletion or insertion and for example can be modified to improve their stability.

The invention also relates to an immunogenic composition comprising recombinant retroviral particles comprising:

1) a recombinant nucleotide sequence containing a defined nucleotide sequence (transgene), placed under the control of regulatory signals of transcription and expression, regulatory signals of retrotranscription, expression and encapsidation and, 2) a polynucleotide encompassing the cis-acting central initiation region (cPPT) and a cis-acting termination region (CTS), these regions being of retroviral or retroviral-like origin or from a transposon and being inserted in a functional orientation and location with retrotranscription regulatory signals of retroviral or retroviral-like origin or with transposons regulatory signals, wherein the immunogenic composition is capable of inducing or of stimulating a CTL (Cytotoxic T Lymphocytes) response against one or several epitopes encoded by the transgene sequence present in the vector.

The DNA fragment encompassing the cPPT and CTS cis-active sequences is able to adopt a three stranded DNA structure the "DNA triplex" after reverse transcription and to stimulate the nuclear entry of the vector DNA.

According to a particular embodiment, the immunogenic composition which is capable of inducing or of stimulating a CTL (Cytotoxic T Lymphocytes) response against one or several epitopes encoded by the transgene sequence present in the vector, comprise recombinant retroviral vector particles comprising:

a) a gag polypeptide corresponding to nucleoproteins of a lentivirus or to functional derived polypeptides (GAG polypeptides), b) a pol polypeptide constituted by the RT, PRO, IN proteins of a lentivirus or a functional derived polypeptide (POL polypeptide), c) an envelope polypeptide or functional derived polypeptides (ENV polypeptides), d) a recombinant nucleotide sequence comprising a defined nucleotide sequence (transgene or a sequence of interest), coding for one or several epitopes, placed under the control of regulatory signals of transcription and expression, a sequence containing regulatory signals of retrotranscription, expression and encapsidation of retroviral or retroviral-like origin and a polynucleotide containing a cis-acting central initiation region (cPPT) and a cis-acting termination region (CTS), these regions being of retroviral or retroviral-like origin and being inserted in a functional orientation with the above-mentioned regulatory signals of retroviral or retroviral-like origin.

According to another embodiment, the immunogenic composition which is capable to induce or to stimulate a CTL (Cytotoxic T Lymphocytes) response against one or several epitopes encoded by the transgene sequence present in the vector comprises recombinant retroviral-like particles which comprise:

a) a polynucleotide containing a cis-acting central initiation region (cPPT) and a cis-acting termination region (CTS), these regions being derived from a retrotransposon and inserted in a functional orientation with retrotransposon regulatory signals, b) a polypeptide corresponding to the nucleoproteins of a retrotransposon or to functional derived polypeptides (GAG polypeptides)

c) a pol polypeptide corresponding to RT, PRO, IN proteins of a retrotransposon or a functional derived polypeptide (POL polypeptide), d) a viral envelope polypeptide, e) a recombinant nucleotide sequence comprising a defined nucleotide sequence (transgene or sequence of interest), placed under the control of regulatory signals of transcription and expression, retrotransposon regulatory signals of retrotranscription, expression and encapsidation.

The recombinant retroviral vector particles which are present in the immunogenic composition replying to one or the other above-definition are in a preferred embodiment capable of inducing, improving or being associated to the occurrence of a memory cell-mediated immune response and especially a memory CTL response.

In accordance with the above disclosed definitions of the immunogenic composition containing the vectors or vector particles can be prepared in accordance with several possible embodiments.

In a preferred embodiment of the invention, the immunogenic composition is prepared in such a way that the sequences of retroviral origin are derived from a lentivirus genome.

According to another embodiment, these sequences are of retroviral-like origin and are derived from retrotransposon.

In another embodiment of the invention, or in addition to the above-defined features, the transgene or sequence of interest which is contained in the recombinant vector is contained in an expression cassette including regulatory signals of transcription and expression.

Alternatively, the regulatory signals of retrotranscription, expression and encapsidation of the vector are of lentiviral origin and the polynucleotide comprising the cPPT and CTS regions is of lentiviral origin.

According to another embodiment, the regulatory signals of retrotranscription, expression and encapsidation and the polynucleotide comprising the cPPT and CTS regions in the vector, are derived from a HIV-type retrovirus, in particular HIV-1 or HIV-2.

Other viruses and especially lentiviruses can be used to design the regulatory signals of retrotranscription expression and encapsidation, and also to derive the polynucleotide comprising the cPPT and CTS regions. Especially, the lentiviruses CAEV, EIAV, VISNA, HIV, SIV or FIV can be used therefore.

For the obtention of the recombinant retroviral particles of the immunogenic composition of the invention, sequences encoding polypeptides or proteins necessary for the transcomplementation of the vectors are for instance GAG, POL and ENV proteins derived from lentiviruses, and especially from HIV, including HIV-1 and HIV-2 retroviruses.

Alternatively, the GAG and POL sequences may be derived from a different virus than the ENV sequence. For instance, GAG and POL sequences can be derived from the HIV retrovirus and the ENV sequence can be derived from another virus or retrovirus, and can be either amphotropic or ecotropic ENV sequences.

In another embodiment, the ENV sequence is derived from the vesicular somatitis virus (VSV).

According to a particular embodiment of the invention, the immunogenic composition which is capable to induce or to stimulate a CTL (Cytotoxic T Lymphocytes) response against one or several epitopes encoded by the transgene sequence present in the vector comprises recombinant retroviral-like particles which comprise:

a) a polynucleotide containing a cis-acting central initiation region (cPPT) and a cis-acting termination region (CTS), these regions being derived from a retrotransposon and inserted in a functional orientation with retrotransposon regulatory signals, b) a polypeptide corresponding to the nucleoproteins of a retrotransposon or to functional derived polypeptides (GAG polypeptides)

c) a pol polypeptide corresponding to RT, PRO, IN proteins of a retrotransposon or a functional derived polypeptide (POL polypeptide), d) a viral envelope polypeptide, e) a recombinant nucleotide sequence comprising a defined nucleotide sequence (transgene or sequence of interest), placed under the control of regulatory signals of transcription and expression, retrotransposon regulatory signals of retrotranscription, expression and encapsidation.

The immunogenic composition of the invention which comprises the recombinant retroviral-like particles are in a preferred embodiment capable of generating a memory cell-mediated response, especially a memory CTL response, in accordance with the above-disclosed features.

The invention also relates to vector constructs which have been deposited with the CNCM (Collection Nationale de Culture de Microorganismes at Institut Pasteur in Paris, France) on Oct. 11, 1999.

A first vector is pTRIP.TEL/AML-IRES-GFP, deposited under number I-2326 on Oct. 11, 1999 and a second vector is designated pTRIP-ILKE-IRES-GFP, and has been deposited under number I-2327 on Oct. 11, 1999.

A third vector, pTRIP.DES-IRES-GFP has been deposited with the CNCM under number I-2331 on Oct. 11, 1999.

The sequences encoding the antigens that are present in the above constructs can be replaced by any other antigen or epitope of interest, including the above cited complete DES gene of M tuberculosis.

According to another aspect of the invention, the vectors, vector particles and immunogenic compositions comprising the same, are designed in such a way that the cPPT and CTS regions are localized centrally within the sequence of the vector.

By <<localized centrally>>, it is meant that the cPPT and CTS regions are in the center of the sequence of the vector, or approximately in the center of this sequence. Especially, the cPPT and CTS regions can be within the central one third of the retrotranscribed linear vector DNA.

The central localization of the triplex sequence formed during viral retrotranscription as a consequence of the presence of the cPPT and CTS sequences enable an improvement of the level of transduction of cells contacted with the vector or vector particles.

Alternatively, according to a variant of the vector, the transcription unit of the vector, including the transgene can be inserted within the U3 region of the LTR region. Accordingly, after retrotranscription, the transgene is duplicated and therefore appears on each side of the triplex sequence, therefore enabling the triplex sequence to be localized at the central position in the vector, whatever the size of the transgene.

The invention also relates to cells which have been put in contact with the immunogenic composition according to the invention and especially relates to recombinant cells transduced by the vector or vector particles of the immunogenic composition.

These cells are advantageously antigen presenting cells. As example these cells can be chosen among lung cells, brain cells, epithelial cells, astrocytes, microglia, oligodendrocytes, neurons, muscle, hepatic, dendritic, neuronal cells, cells strains of the bone marrow, macrophages, fibroblasts, hematopoietic cells.

The immunogenic composition of the invention can thus be used in treatment protocols or for the preparation of treatment compositions for the therapeutic treatment of tumors and especially of cancer, either to generate a primary cell-mediated immune response, especially a CTL response which is advantageously a memory CTL response. Alternatively, it can be used as an adjuvant treatment with other known anticancer treatment.

For instance, the immunogenic composition of the invention can be used in association with chemotherapy or immunochemotherapy or other approaches to anticancer treatment.

By the expression <<anticancer treatment>>, it is intended in accordance with the present invention, the inhibition of growth of the tumor or potential growth of the tumor or the inhibition of spread of the malignant cells, including the possibility of controlling formation of metastasis, or both.

Therefore, according to the invention, the expression <<anticancer treatment>> relates to protocols that are used to control the malignant growth and spread of tumors, do anticipate recurrence of the disease, especially in view of the fact that the immunogenic composition is capable of inducing or improving, and in general participating to, a memory cell-mediated response.

Tumors that may be treated with the compositions of the invention, are for instance melanomas or carcinomas including (lung, bladder, renal, colon) and Lymphoproliferation.

The tumors that may be treated are also all the tumors expressing tumor specific antigens including self protein mutated and/or self protein surexpressed.

Every possible acceptable ways of administration of the immunogenic composition of the invention are of interest including administration protocols comprising ex vivo steps, for instance ex vivo transduction of target cells followed by administration of the treated cells to the patient to be treated.

Alternatively, the immunogenic composition according to the invention can be directly administered to the patient through usual routes of administration, including systemic (IV), locally, or cutaneously, intradermic, for instance intratumoral, administration routes.

In a particular embodiment, the immunogenic composition according to the invention can be directly administered to the patient, in such a way that it will induce, improve or participate in vivo to the occurrence of a cell-mediated immune response, especially a CTL-mediated immune response.

In another embodiment, the immunogenic compositions are used so that they can enable the occurrence of a long-term memory cell mediated response.

It is emphasized that the immunogenic composition of the invention has a particular interest due to the property of the cPPT and CTS sequences which are present in the vector and vector particles, to induce or to stimulate the nuclear import of the vector genome in the target cells.

A particular advantage of the immunogenic compositions of the invention is that they can be used to elicit or stimulate a cell-mediated immune response against multiple epitopes encoded by the nucleotides sequence of interest or transgene present in the vector or vector particles, and they can also be used to elicit or stimulate a cell-mediated immune response against the product of the entire sequence of a gene, for instance a gene of a pathogenic agent or fragments of said gene capable to encode at least 8 to 15 amino acids preferably 9 to 12 amino acids. The invention covers also a nucleotidic sequence comprising nucleotidic sequence encoding a multiple repeat (at least 2 identical sequences) of said amino acid sequence inducing a cellular response and/or an amino acid sequence containing at least 2 different sequences corresponding to 2 epitopes of different pathogens or tumoral antigens.

Other characteristics or advantages of the invention are disclosed in the following examples and drawings.

Melanoma specific CTLs mono or polyepitopical sequences

Construction of HR.MEL-IRES-GFP

To construct the HL.MEL-IRES-GFP plasmid, the Ndel/Xhol fragment of TRIP.MEL-IRES-GFP deposited at the CNCM under n° 1-2185 on Apr. 20, 1999 containing part of the CMV promotor, the polyepitope MEL and the IRES-GFP instead of Ndel/Xhol fragment of HR GFP containing a part of the CMV promotor and the GFP.

FIG. 6: Restriction Card of pTRIP.ILKE-IRES-GFP vector

HIV specific CTLs mono or polyepitopical sequences, the epitope of which 19V.(ILKE); (RT 476-484)

Construction of TRIP.ILKE-IRES-GFP (deposited at the CNCM, Paris, France on Oct. 6, 1999 under n° . . . .

TRIP.ILKE-IRES-GFP was constructed by inserting the PCR product of ILKE into TRIP ΔE IRES-GFP, between the CMV promotor and the IRES. The region surrounding the CTL epitope beginning by ILKE was amplified by PCR on the matrix pLAI with the primers:

5 ILKE:
(SEQ ID NO: 1)
5TCAGATCTGCCACCATGGCACTAACAGAAGTAATACCAC 3'

3 RIILKE:
(SEQ ID NO: 2)
5' CGGAATTCTTATTGGCCTTGCCCCTGCTTC 3'.

A Kozak sequence was inserted into the upstream primer and a stop codon was inserted into the downstream primer.

After digestion of with BglIII/Eco RI the PCR product was inserted into TRIP ΔE IRES-GFP into the BamHI/EcoRI sites.

The vector expresses a bi-cistronic messenger coding for GFP and a region of the RT gene of VIH, corresponding to a cluster of epitopes, comprising especially the 19V epitope (RT 476-484) restricted to HLA.A2.1 (Walker B. D., 1989 PNAS 86p. 9514-9518).

Figure 7:
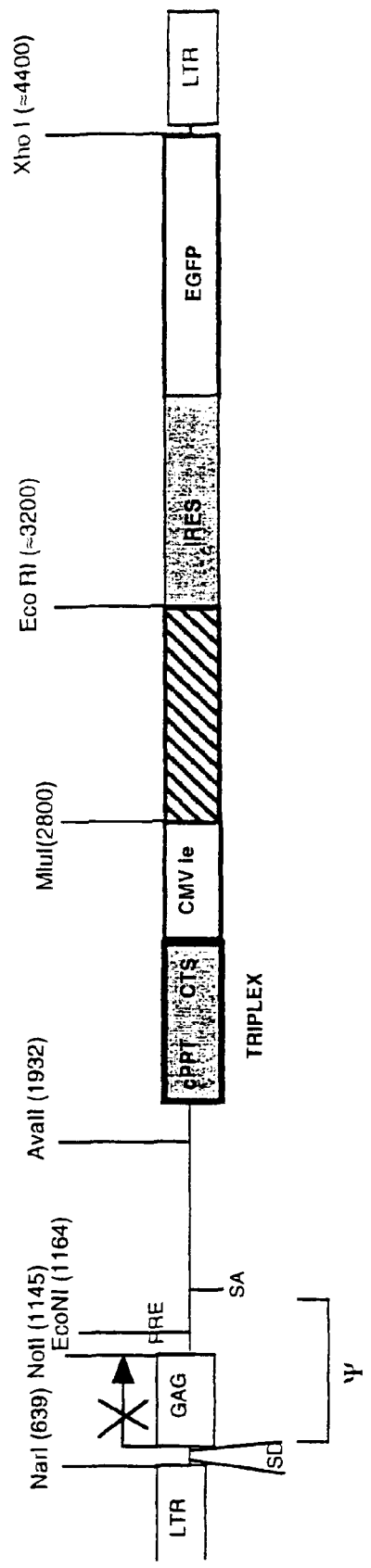

FIG. 7: Restriction Map of pTRIP.TEL/AML-IRES-GFP vector

Translocation TEL/AML Sequence

TRIP.TEL/AML-IRES-GFP was constructed by inserting the PCR product of TEL/AML into TRIP ΔE IRES-GFP, between the CMV promotor and the IRES. The region surrounding the translocation between TEL and AML was amplified by PCR with the primers:

5 Bgl TA:
(SEQ ID NO: 3)
5'GAAGATCTGCCACCATGAAGCCCATCAACCTCTCTCAT 3'

3 RITA:
(SEQ ID NO: 4)
5' CGGAATTCTTACCCAGCGCAACGCCTC 3'

A Kozak sequence was inserted into the upstream primer and a stop codon was inserted into the downstream primer.

After digestion of with Bgl II/EcoRI the PCR product was inserted into TRIP ΔE IRES-GFP into the BamHI/EcoRI sites.

Figure 8A:
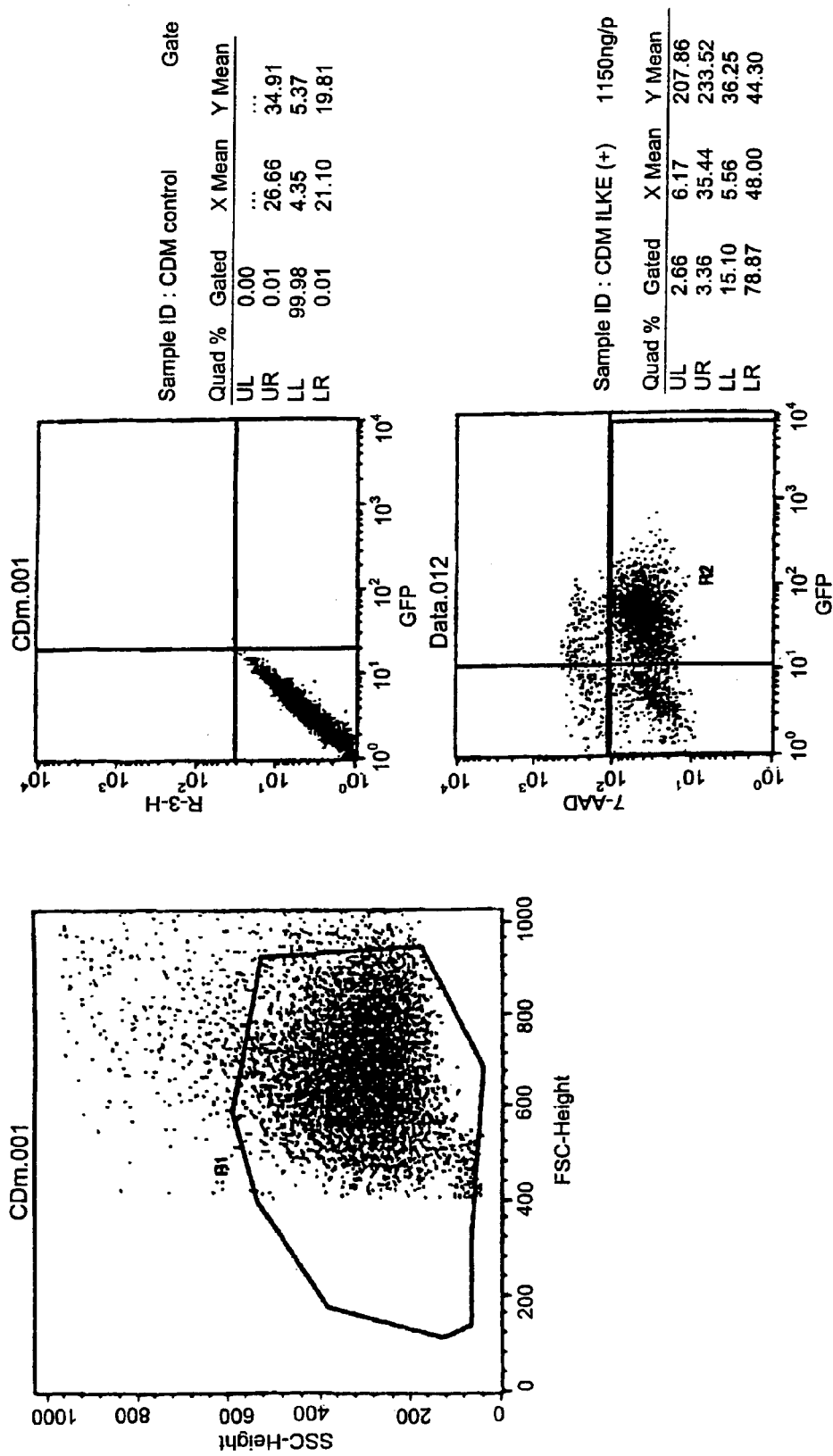
Figure 8B:
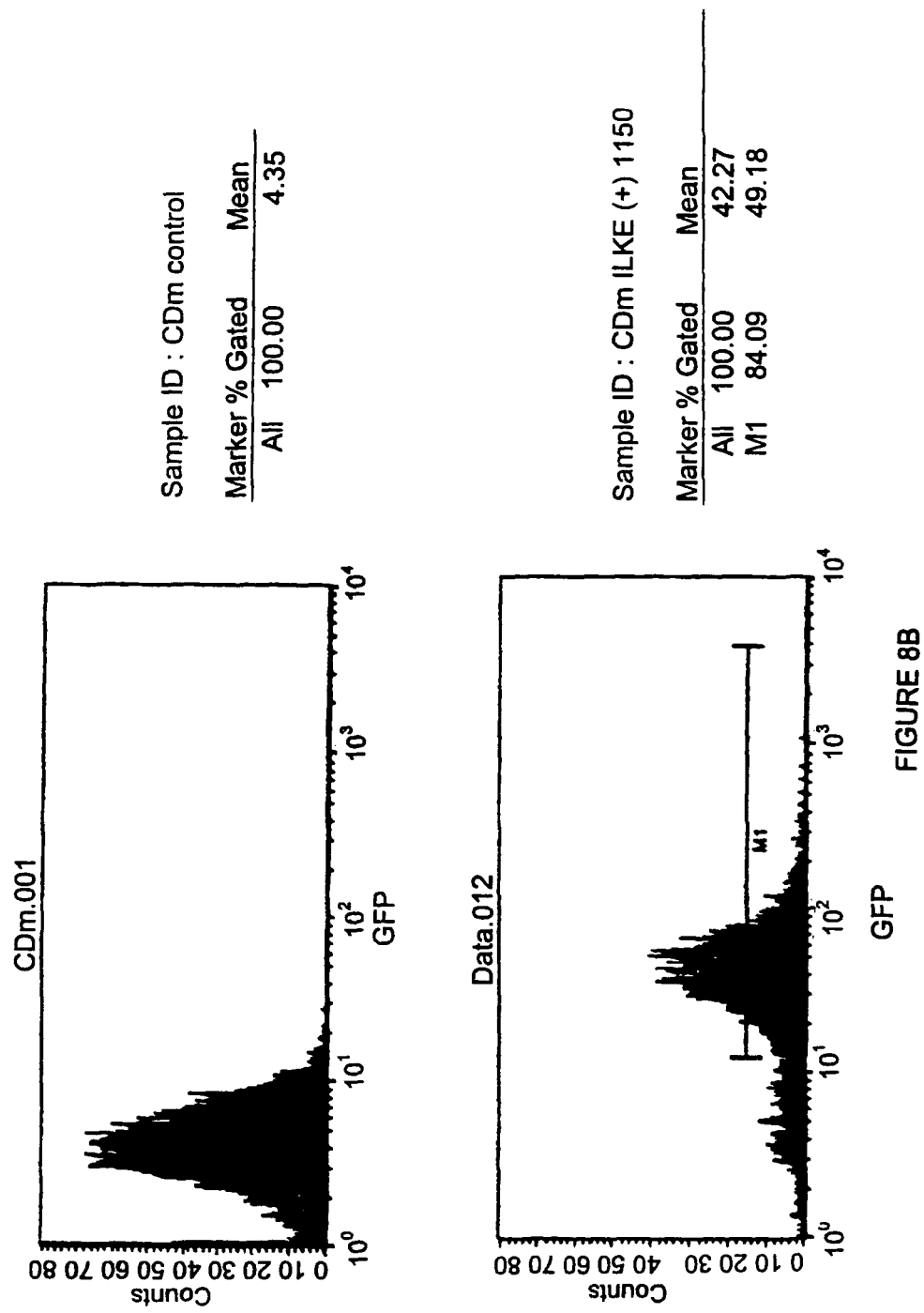

FIGS. 8 A and B: Transduction capacity of HIV-derived DNA triplex positive vector encoding 19V epitopic peptide (derived from HIV 1 pol) and GFP of murine dendritic cells that were produced using bone marrow cells from HHD transgenic mice. A) Gating. B) GFP Expression.

About 80% of murine dendritic cells are transduced by the HIV derived triplex positive recombinant vector as documented by FACS analyses of intra cellular GFP expression.

FIG. 9: Evaluation of CTL responses in HHD mice after immunization with the TRIP-des-IRES-GFP vector encoding the DES gene of Mycobacterium tuberculosis.

Figure 10:
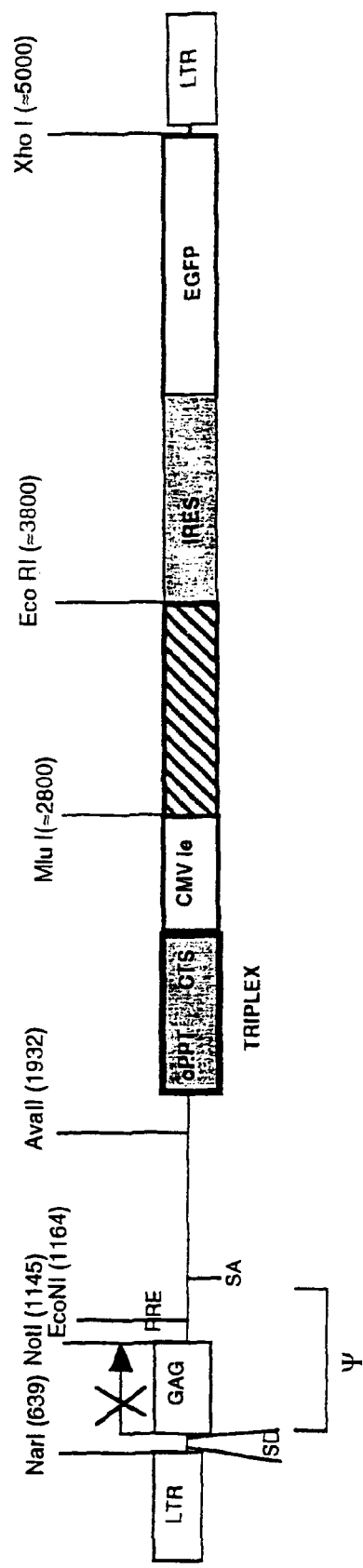

FIG. 10: Restriction map of pTRIP.DES-IRES-GFP deposited with the CNCM on Oct. 11, 1999.

EXAMPLES

Lentiviral vectors have the capacity to transduce cells, including non dividing cells, and are increasingly proposed for gene therapy. Recently, we showed that lentiviral vectors containing the polypurine tract cis-acting sequence (central DNA triplex) exhibit more efficient transduction of human and murine cells than those deleted for the central DNA triplex (Charneau P. et al, J. Mol. Biol. 1994, 241, 651-662). Lentiviral vectors containing or not central DNA triplex and encoding the same HLA-A2.1 restricted melanoma CTL polyepitope have now been tested for their capacity to induce CTL responses. The direct in vivo administration of the lentiviral vector containing central DNA induced strong CTL responses against all epitopic peptides encoded by the polyepitopic sequences in HHD <<HLA-A2.1 pure>> mice. A clear advantage was shown for the lentiviral vector containing the DNA triplex. Furthermore, we showed that the lentiviral vector containing the DNA triplex transduce the human dendritic cells up to 7-fold more efficiently than the vector not containing the triplex. These ex vivo transduced dendritic cells elicited efficient specific primary CTL responses against most of the melanoma epitopic peptides. Since the safety concern of modified lentiviral vector has been mostly resolved, we propose the use of that vector not only for in vivo human gene therapy, but also for immunotherapy of cancer patients.

Introduction

The Lentiviridae subclass of retrovirus can infect most cell types including non-dividing cells. This property makes lentivirus attractive for gene therapy. Several replication-defective recombinant lentiviral vectors have already been constructed by different groups (Naldini PNAS 93, 11382-8, Science, 1996). These reengineered and detoxified lentiviral vectors are proposed as the most efficient and safe gene therapy vectors (Zufferey R, & Kim V. N. J Virol, 72, 9873-80, 1998). We developed a human lentiviral (HIV)-based vector, pseudotyped with vesicular stomatitis virus G glycoprotein (VSVG) (Burns J. C., 1993 PNAS 90, 8033-7). This vector was deleted for most of the non essential viral proteins but contains a polypurine tract cis-acting sequence (cPPT, central DNA triplex). The central DNA triplex considerably enhances the nuclear import of retrotranscribed HIV-DNA molecules. Moreover, it was observed that the lentiviral vector containing the central DNA triplex displays more efficient transduction of murine and human cells in vitro than the vector not containing the triplex.

The HHD <<HLA-A2.1 pure>> transgenic mouse (Pascolo et al., J. Exp. Med., 1997, 185: 2043-2051) allow for an experimentally controlled evaluation of the immunogenic potential of epitopic peptides and of various immunisation strategies. Using these HHD mice, the capacity of a melanoma polyepitope encoded by different recombinant vectors to induce simultaneous CTL responses within a single animal has been reported. The capacity of lentiviral vectors containing or not central DNA triplex and encoding the same melanoma polyepitope for in vivo CTL induction in HHD transgenic mice has first been studied. Furthermore, it was also investigated whether human dendritic cells (hDC) transduced by the same recombinant lentiviral vectors induce primary CTL responses against the melanoma polyepitopic motive ex vivo. The present results demonstrate that the DNA triplex enhances significantly the capacity of lentiviral vector to induce specific CTL responses in vivo by direct administration of the recombinant vectors or ex vivo using transduced dendritic cells.

Results

Example I

Melanoma Polyepitopic Immunisation

Figure 1:
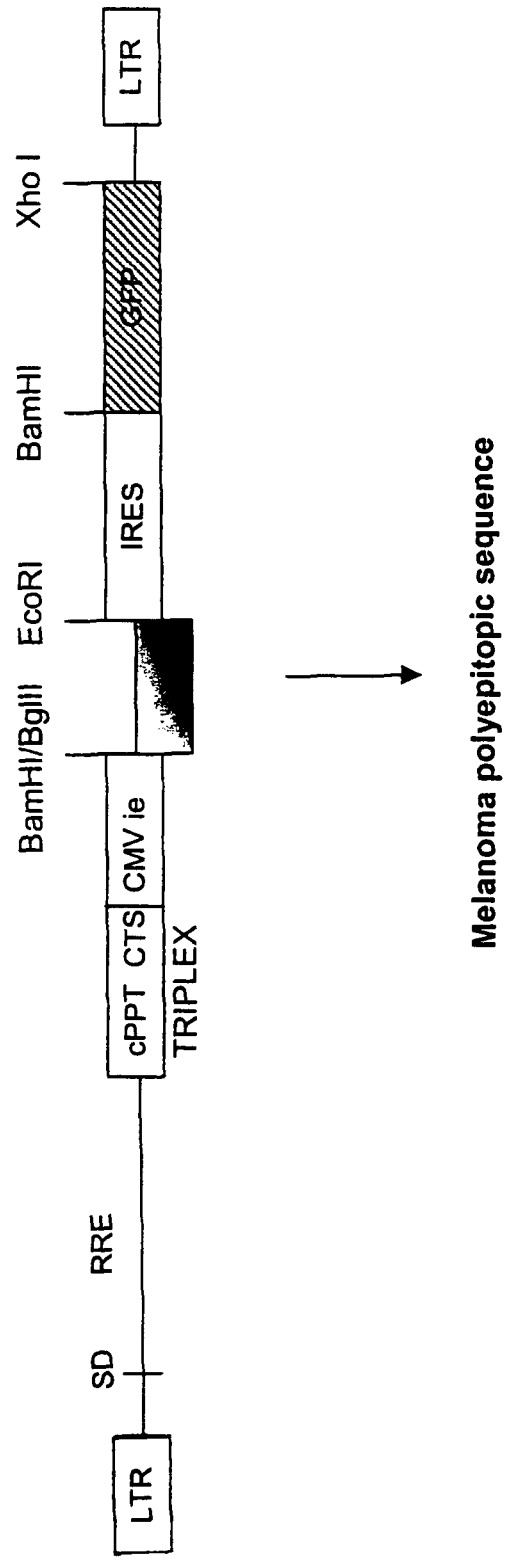
FIG. 1: HIV1-derived triplex DNA positive recombinant vector encoding a melanoma polyepitope (SEQ ID NO:11).

After establishing that injection of recombinant-DNA encoding a melanoma-derived polyepitopic motif can elicit simultaneously CTL responses against several melanoma epitopes in HHD mice, the immunogenic capacity of a lentivirus vector encoding the same melanoma polyepitopic motive (FIG. 1 and Table 1) was tested. A TRIP-mel-IRES-GFP vector (CNCM 1-2185 deposited on Apr. 20, 1999) was administered at 1.25 µg/p24 per mouse either intravenously, intra peritoneally, or subcutaneously. At least 3 mice per group were used.

Multiple specific CTL responses were simultaneously induced against most of the ten melanoma epitopes. Similar CTL responses were observed regardless of the route of administration against both peptide loaded (Table 2) and TRIP-mel-IRES-GFP transduced, HHD-transfected HeLa cells (data not shown). However, intraperitoneal injection induced slightly better CTL responses. Strong responses were elicited against NA17-A.nt38 and gp 100.154 epitopic peptides. Significant responses were also observed against gp100.457, MART.1.27, Mage-3, and Tyrosinase.368-D. CTL responses were weak against gp100.209, gp100.280, MART-1.32, and Tyrosinase.1. The epitopes which elicit weak CTL responses following TRIP-mel-IRES-GFP vector immunisation all fall into the non CTL-inducer groups when administered using other non lentiviral vectors.

Minimal Lentiviral Vector Dose Required for In Vivo Detectable CTL Induction

Figure 3:
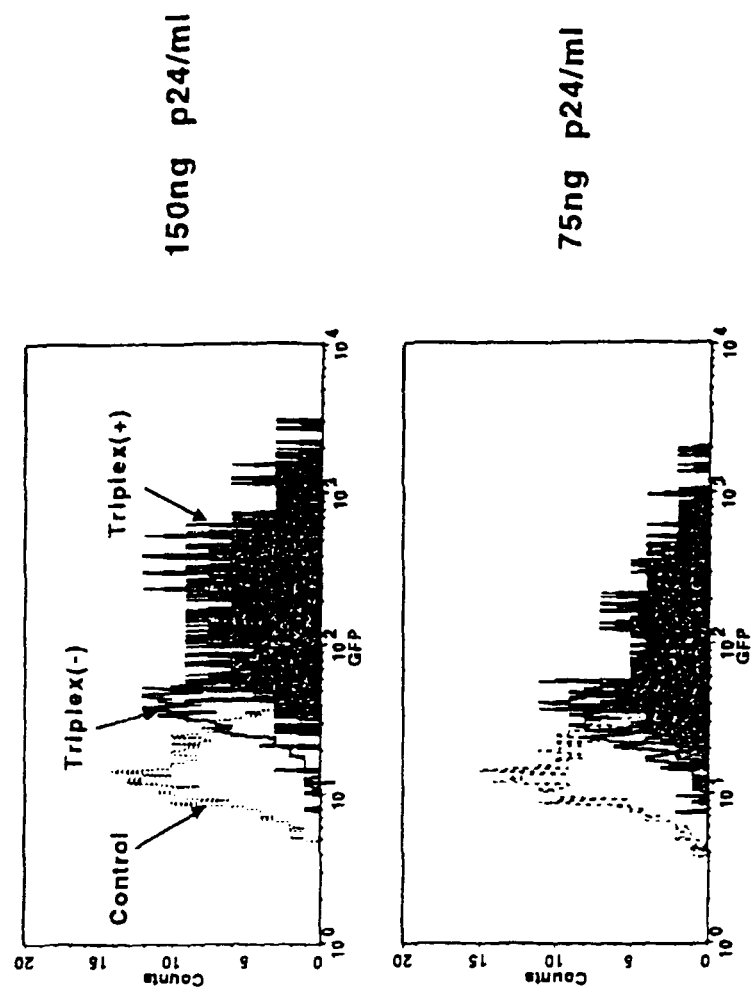
FIG. 3: GFP expression in human cells 5 days after their transduction by the central DNA triplex positive or negative HIV1-derived vectors.

The minimal lentiviral vector dose eliciting a significant CTL response was determined in HHD mice using intraperitoneal injections of TRIP-mel-IRES-GFP vector at six different doses using 4 mice per dose. Two experiments were performed in which effector cells of two mice were mixed to have similar E/T ratios just before the $^{51}$Cr test. In most experiments CTL responses were tested against all melanoma epitopic peptides. Because the results were highly similar and very homogeneous, only CTL responses against NA17/A epitopic peptide were taken into account to compare <<dose-effect>> relationship for the sake of clarity and simplicity. The best CTL responses were obtained using doses between 500 ng and 2500 ng/p24 per mouse (Table 2). Although detectable CTL responses were obtained against some of the melanoma epitopes, high lentiviral doses did not induce better CTL responses than low doses. Eventhough, some specific CTL responses against some of the melanoma epitopic peptides were evidenced, doses below 500 ng/p24 per mouse were not sufficient to induce efficient CTL responses. It is noteworthy that at the dose of 1250 ng/p24 per mice, some mouse generated CTL responses against ten out of ten epitopes included in the polyepitopic motif (FIG. 3).

Long Term Memory CTL Induction

Figure 2:
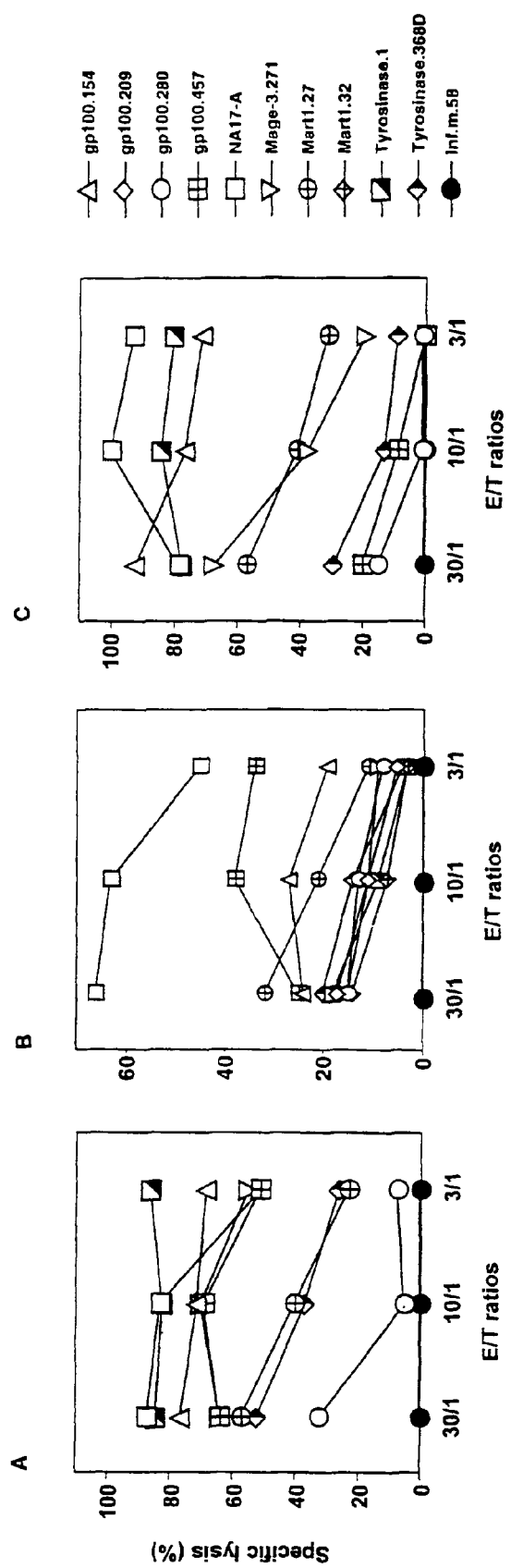
FIG. 2: CTL responses of HHD mice after immunization with the TRIP-mel-IRES-GFP vector.

Eight mice were injected with the TRIP-mel-IRES-GFP vector. The mice were sacrificed either 12 days or 5 months after immunization. After 5 days in vitro stimulation with the melanoma epitopic peptides and two additional day with 10% TCGF, effector cells of four mice were mixed and tested against peptide loaded HHD-transfected RMAS cells. Specific CTL responses were evidenced for all melanoma epitopic peptides but for gp100.209 and Marti 0.32 in mice immunized 12 days before. Five months after injection of the TRIP-mel-IRES-GFP, all of the primary CTL inducer epitopes still induced strong CTL responses (FIG. 2). The level of CTL responses 12 days or 5 months after immunization of mice was surprisingly comparable. This suggests that in vivo transduced cells by the lentiviral vector are not destroyed by the immune system and continue to produce the encoding melanoma polyepitope.

Role of the Central DNA Triplex for In Vivo Immunisation

HHD mice were immunised individually at the same time with the TRIP-mel-IRES-GFP and HR-mel-IRES-GFP vectors administered intraperitoneally at doses of 800 ng, 200 ng, 50 ng, 12 ng, and 3 ng/p24 per mouse. At least four mice were tested for each dose in two separate experiments. After in vitro stimulation by synthetic peptides, the cytolytic capacity of spleen cells was tested using peptide pulsed RMAS-HHD target cells. Because the results were highly homogeneous, only CTL responses against NA17/A, Mart-1.27, gp100.154, and Tyrosinase.368-D epitopic peptide were tested for the sake of clarity and simplicity.

The results are illustrated in Table 3. In general, the mice immunised with the TRIP-LV vector at doses of 800 ng, 200 ng, and 50 ng/p24 per mouse, elicited better CTL responses than the mice immunised with the HR-LV vector. There was no detectable CTL response at the dose below 12 ng/p24 per mouse regardless of the vectors used (data not shown). This confirms the enhanced transduction capacity of lentiviral vectors containing the central DNA complex in comparison with those lacking this complex.

Dendritic Cells Transduction by the Lentiviral Vectors

It was initially observed that tumor cells such as MT4 and HeLa cells can be transduced up to 30-fold more efficiently by the lentiviral vector containing the central DNA triplex than by the vector lacking the central DNA triplex. The transduction capacity of these two lentiviral vectors at different concentrations was then tested on DC from healthy donors or from HHD mice. The percentage of DC expressing GFP and their mean intensity of fluorescence were measured by FACS and considered as the transduction level of DC by the two lentiviral vectors.

Figure 4:
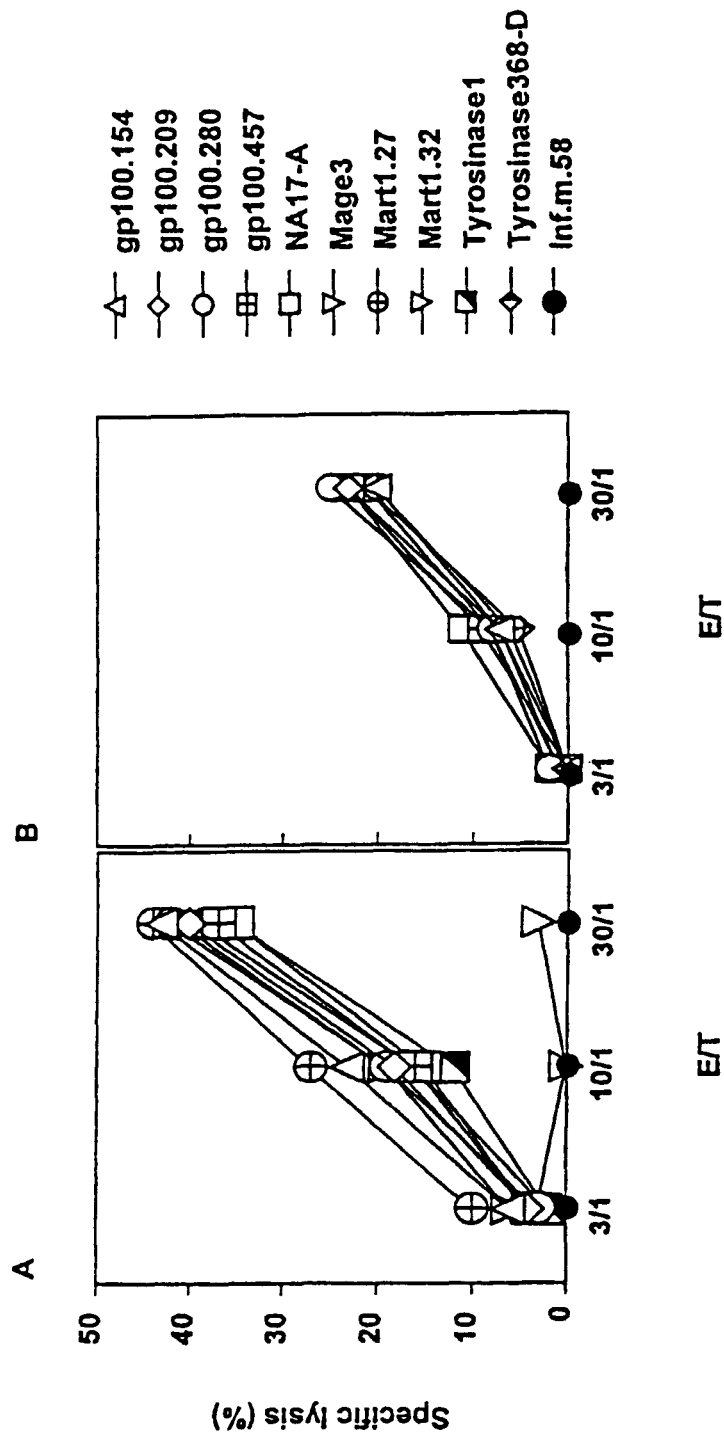
FIG. 4: In vitro CTL responses using human dendritic cells.

The TRIP-GFP vector transduced the cells more efficiently than the HR-GFP vector at all vector concentrations. The GFP expression of murine and human DC transduced by the TRIP-GFP vector was respectively up 3- and 7-fold higher than the expression of those transduced by the HR-GFP vector (FIG. 4).

Primary CTL Induction Using Human Dendritic Cells Transduced by TRIP mel IRES-GFP Vector Mononuclear cells (MNC) obtained from healthy HLA-A2.1 donors were stimulated in vitro once a week using the DC from the same donor transduced by TRIP mel-IRES-GFP. The presence of GFP expression in the dendritic cells was analysed by FACS to verify efficient transduction. After three weeks, the cytotoxic capacity of the MNC was tested in a $^{51}$Cr assay using peptide pulsed T2 cells as targets in FCS free culture condition.

Figure 5:
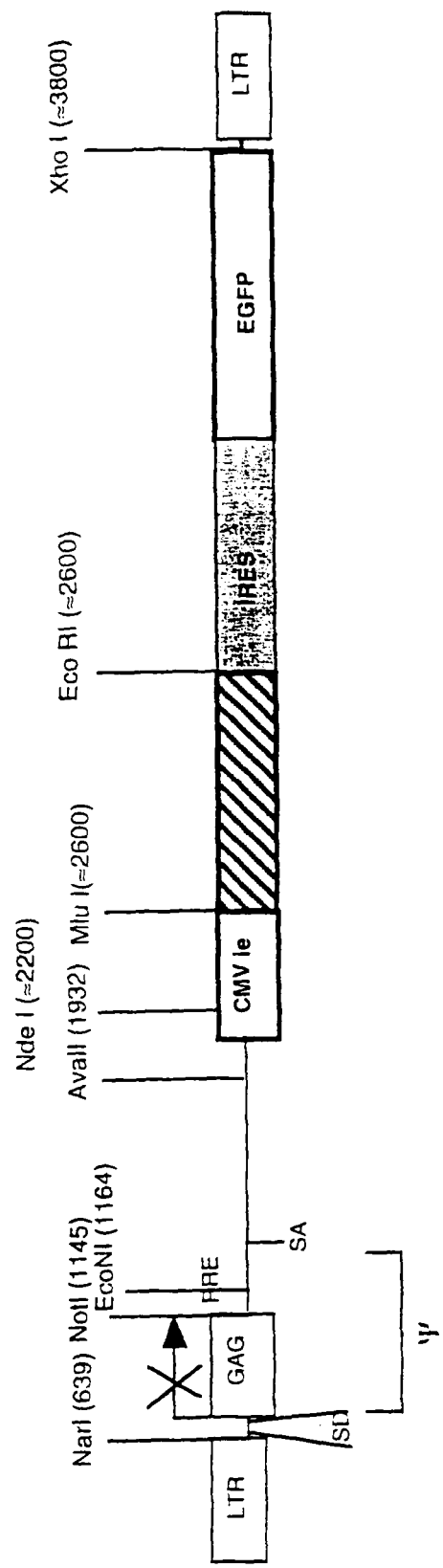
FIG. 5: Restriction Card of pHR.MEL-IRES-GFP vector

The hDC transduced with the TRIP-mel-IRES-GFP vector induced significant CTL responses against all melanoma epitopic peptides but Marti 0.31, whereas non transduced hDC induced only habitual background responses (FIG. 5).

Discussion

Recent reports show that replication defective lentivirus derived vectors can transduce a variety of nondividing cells (Naldini, 1996, Kafri, 1997) Lentivirus can enter through the intact nuclear membrane of nondividing cells (Case, 1999). We have now evidenced that this procedure is largely orchestrated by a polypurine tract cis-acting sequence, denominated the central DNA triplex. Introduction of this sequence into the lentiviral-derived vectors allowed for up to 30-fold higher in vivo and ex vivo stable transduction of several cell types including neurons, hepatocytes, and hematopoietic stem/progenitor cells.

Recently, progress has been accomplished to address the safety concern of lentivirus-derived vectors and their use in gene therapy (Narry Kim V et al 1988, Zufferey, 1999). However, lentiviral vectors have never been studied for immunotherapy applications for which classical murine retroviral vector and non retroviral vectors were successfully used (Condon, 1996, Song 1997, Specht, 1997). To develop a potent vaccine strategy, the immunogenic capacity of a lentiviral vector containing the central DNA triplex and encoding a melanoma polyepitope has been tested. Direct injection of this vector was first studied to assay whether it can elicit in vivo specific CTL responses against the melanoma epitopes. Previously several immunisation strategies in HHD HLA-A2.1 <<pure>> transgenic mice were compared. Using recombinant pCMV-B10 (HBs) DNA or recombinant vaccines encoding the same melanoma polyepitope, it was possible to simultaneously induce, in a single mouse, CTL responses against fout to six different peptides included in the melanoma polyepitope. For the TRIP mel IRES-GFP vector encoding the same melanoma polyepitope, we obtained significantly better results than with other vectors encoding the same polyepitopic motive in terms of specific lysis but also in terms of number of peptides eliciting CTL responses. Particularly, intraperitoneal and subcutaneous injection of vector induced in some mice CTL responses against all epitopes encoded by the TRIP mel IRES-GFP vector.

Several groups reported that dendritic cells which are transduced or peptide loaded can be used as a potent immunisation approach against a variety of cancer cells (Mayardomo, JI, 1995, Song W, 1997, Specht, J M, 1997). For the purpose of this invention, it was therefore studied whether murine and human dendritic cells can be transduced efficiently and induce primary CTL responses in vitro. The present results clearly demonstrate that these cells can easily be transduced. Furthermore, these transduced cells presented all epitopes encoded by the recombinant lentiviral vector. Interestingly, human dendritic cells were most easily transduced probably. In vitro transduction of the cells prevents the lentiviral vectors to integrate their genome into a variety of host cells in a hazardous manner. For this reason, in vitro transduced cells should constitute an appropriate and safe delivery method for a first clinical application.

Warner et al were first showing the capacity of retroviral vector to induce efficient CTL responses in several animal models but also in HIV patients using murine retroviral vector-transduced fibroblast expressing HIV-1 proteins (reviewed by Warner 1998). Injected directly into the mouse, proviral DNA were detected in dendritic cells which present antigens efficiently (Song, 1997). However, in contrast to the lentiviral vectors, the murine retroviral vectors can not transduce non-dividing cells such as DC and in vivo expression of the encoding gene is often subject to <<shut off>>. Consequently, these retroviral vector are not the best candidate for human immunotherapy (Kafri).

Our results demonstrate clearly that lentiviral-derived vectors containing the central DNA triplex induce stronger CTL responses in vivo in HHD mice than those not containing the central DNA triplex. Furthermore, lentiviral vector containing the central DNA triplex can easily transduced hDC in vitro which could be subsequently used for clinical immunotherapy.

Materials and Methods

Lentiviral Vector Constructions

Vector plasmids: pTRIP-EGFP derived from HR'CMVLacZ (Naldini et al, PNAS 93, 11382-8, 1996). LacZ reporter gene was replaced by the EGFP gene (Clontech). In TRIP-EGFP, the EGFP gene was inserted in the ClaI site of a central fragment of HIV-1 LAI comprising cPPT and CTS sequences.

EGFP gene was amplified by PCR using Pfu polymerase (Stratagene) from pEGFP-N1 plasmid, adding BamHI and XhoI restriction sites in 5' and 3' respectively. PCR primers were as follows:

```
Bam GFP
                                    (SEQ ID NO: 5)
5' CC GGATCC CCA CCG GTC GCC ACC 3'

Xho GFP
                                    (SEQ ID NO: 6)
5' CC CTCGAG CTAGAG TCG CGG CCG 3'.
```

HR GFP vector was constructed by cloning back this PCR fragment into BamHI and XhoI sites of pHR'CMVLacZ, replacing the LacZ ORF by EGFP.

A 178 bp fragment of pLAI3 (4793 to 4971), encompassing cPPT and CTS, was amplified by PCR. NarI restriction sites were added in 5' of the primers in the aim to insert this fragment into the unique ClaI site of HR GFP:

```
Nar TRIP-F+:
                                       (SEQ ID NO: 7)
5' GTC GTC GGCGCC GAATTC ACA AAT GGC AGT ATT CAT
CC 3'

Nar TRIP-:
                                       (SEQ ID NO: 8)
5' GTC GTC GGCGCC CCAAAG TGG ATC TCT GCT GTC C 3'.
```

Insertion of this triplex sequence in the correct orientation gave rise to the TRIP GFP plasmid vector, and TRIPinv GFP in the reverse orientation. Alternatively, the same triplex fragment was amplified from pcPPT-AG, pcPPT-D, pcPPT-225 and pCTS plasmids to generate vectors including the same mutations in the cPPT or in the CTS as the corresponding viruses.

First, the EcoRI site present in the TRIP GFP vector or TRIP-EGFP (deposited at the CNCM under n° I-2005 on Apr. 15, 1998) was filled, creating the TRIP GFP ΔE vector. Then a 1.2 Kb BamHI/XhoI fragment containing the internal ribosome entry site (IRES) of a picornavirus was cloned up-stream the EGFP instead of the 0.7 kb BamHI/XhoI EGFP in a TRIP GFP ΔE vector, creating the TRIP ΔE IRES GFP vector. The sites present between the CMV promotor and the IRES GFP sequence are BamHI-BstXI-SnaBI and EcoRI. A CTL polyepitope melanoma (mel) fragment was generated by PCR on the pBS mel poly, inserting a kozac consensus sequence inside the primers

```
BglMlu Mel:
                                       (SEQ ID NO: 9)
5'CCAGATCTACGCGTGCCACCATGGCTGCTGGT 3'

3RIMel:
                                       (SEQ ID NO: 10)
5'CGGAATTCGACCTAAACGCAACGGATG 3'.
```

The mel PCR fragment was digested by BglII/EcoRI and inserted in the BamHI/EcoRI sites of TRIP ΔE IRES GFP, creating the TRIP ΔE mel IRES GFP also called TRIP mel IRES GFP.

The HR mel IRES GFP was created by exchanging the NdeI/XhoI fragment containing the melanoma polyepitope and the IRES GFP of TRIP mel IRES GFP with that of HR GFP. The NdeI site is situated at the end of the CMV promotor.

Production of Viral Vectors.

The lentiviral vectors were produced as described previously (Naldini I. M. PNAS 1996 and science 1996) by a transient tree-plasmid transfection of 293T cells using the phosphate-calcium technique. Briefly, 293T cells were transfected with 20 μg of the VSV envelope plasmid (pMDG) and 40 μg of the various packaging (8.2 or 8.91) and lentiviral vector plasmids. Conditioned media were collected 60 h and 84 h after transfection. The virus was then concentrated and dNTPs were treated as previously described (Naldini science 1996). Viral titres on HeLa P4.2 cells and MT4 cells were determined by serial dilution and p24 ELISA assay (Naldini Science 1996).

One cycle titration of viruses were performed in triplicate by infection of P4 cells plated in 96 well plates, with equivalent amounts of particles (1 ng of p24 viral antigen per well), in the presence of 20 μM of DEAE-dextran. The protease inhibitor Saquinavir (Roche), was added at 1 μM throughout the experiment, to restrict the analysis to a single cycle of infection. Cell mitosis was inhibited by aphicolin treatment (8 μM), the day prior infection. The p-galactosidase activity was measured 48 h after infection using a chemiluminescent n-Gal reporter gene assay (Boehringer).

HeLa cells were infected in triplicate with equivalent amount of vector particles (5 ng P24 per well). At 48 hours post transduction, medium was replaced by 200 μl of TNB (Tris 50 mM pH 7.5, NaCl 150 mM) and fluorescence of living cells quantitated using a microplate fluorimeter (Victor$^2$, Wallac) and EGFP adapted filters (excitation: 485 nm, emission: 520 nm).

Mice. HHD mice have been described previously (Pascolo, 1997). They express a transgenic monochain histocompatibility class I molecule in which the C terminus of the human b2m is covalently linked by a peptidic arm (GGGGS)×3 to the N terminus of a chimerical heavy chain (HLA-A2.1 a1-a2, H-2D$^D$ a3—transmembrane, and intracytoplasmic domains). The H-2D$^b$ and mouse b2m genes of these mice have been further disrupted by homologous recombination resulting in complete lack of serologically detectable cell surface expression of mouse histocompatibility class I molecules.

Generation of hDC and Primary CTL Induction.

Human dendritic cells were obtained from cytapheresis products of healthy donors of HLA-A2.1 haplotype (IDM, Paris, France). FACS analysis of these DC using mAbs against CD3, CD14, CD80, CD83, HLA-ABC, and HLA-DR showed immature DC phenotype. The hDC were transduced in 1 ml AMV-5 culture medium with the lentiviral vectors at concentrations of 600 ng, 300 ng, 150 ng, and 150 ng/p24 per $1 \cdot 10^6$ cells for ten days. The percentage and mean fluorescence intensity of GFP expression in hDC transduced with the two lentiviral vectors were measured by FACS (Becton Dickinson, BD, USA).

Mononuclear cells (MNC) from the same donor were stimulated in vitro by the hDC or transduced hDC with a ratio of 4 MNC to 1 hDC. The MNC were restimulated twice using the same cryopreserved-transduced hDC and then tested for cytolytic activity in a 4 h $^{51}$Cr-release assay, using as targets T2 cells loaded with relevant or negative control (Inf.m.58) peptides (10 μg/ml, $5 \cdot 10^6$ cells/ml, in FCS-free RPMI medium, 2 h at RT).

Generation of Murine Dendritic Cells

Bone marrow-derived dendritic cells were generated as previously described [43, 51]. Bone marrow mononuclear cells were cultured in RPMI supplemented with 10% FCS, 2 mM L glutamine, 50 U/ml penicillin, 50 μg/ml streptomycin, $5 \cdot 10^5$ M 2-mercaptoethanol (complete RPMI medium), further supplemented with 20 ng/ml recombinant mouse GM-CSF and 100 ng/ml recombinant mouse IL4 (both from GENZYME, Cambridge, Mass.). On day 2 and 6, non adherent cells were carefully removed, and fresh complete RPMI medium, supplemented with 10 ng/ml mouse GM-CSF and 50 ng mouse IL4, was added. On day 7, the culture medium was replaced by 1 ml complete RPMI medium supplemented with the lentiviral vectors at concentrations of 600 ng, 300 ng, 150 ng, and 150 ng/p24 per $1 \cdot 10^6$ cells. Dendritic cells collected on day 9 were more than 95% pure (IA$^{b+}$, HHD$^+$, CD3", 33D1$^+$, NDL145$^+$, and CD 11c$^+$), as assessed with appropriate mAb. Percentage and mean intensity of fluorescence of GFP expression in murine DC was then measured at day 9 and 12 by FACS.

Vector Immunization and In Vitro Restimulation and Cytolytic Assays

HHD mice were injected either intraperitoneally, intravenously or subcutaneously with lentiviral vectors for 12 days. Spleen cells from primed mice were then individually restimulated in complete RPMI medium by each epitopic peptide for seven days. The last two days, the cultured cells were restimulated by 10% TCGF. On day 7, cultured cells were tested for cytolytic activity as already described (Pascolo, 1997), in a 4 h $^{51}$Cr-release assay, using as targets HHD-transfected TAP-RMA-S cells loaded with relevant or negative control (Inf.m.58) peptides (10 μg/ml, 5·10$^6$ cells/ml, in FCS-free RPMI medium, 2 h at RT). The TRIP-mel-ITES-GFP transduced or non transduced HHD-transfected HeLa cells were parallely used as target cells. The percentage of specific lysis was calculated as follows: (experimental release−spontaneous release)/(total release−spontaneous release)×100.

Example II

Evaluation of CTL Responses in HHD Mice after Immunization with the TRIP-Des-IRES-GFP Vector Encoding the DES Gene of Mycobacterium Tuberculosis The DES gene is disclosed in WO 98/04711.

Experimental Procedure

In a first step, the TRIP-des-IRES-GFP vectors were used to transduce HeLa-HDD cells. These cells were transduced and cloned by limiting dilution. The clone expressing the higher level of GFP was selected to use as target cells in classical $^{51}$CrCTL tests.

In a second step, HDD mice were injected intraperitoneously using 1.2 micg/p24 per mouse of the TRIP-des-IRES-GFP vector particles. Spleen cells of these mice were in vitro stimulated at 12 days post-injection with either 0.2 micg, or 1 micg/p24/ml (2 10$^6$ cells per ml) of vector particles or with TRIP-des-IRES-GFP transduced, LPS stimulated syngeneic blast cells with 1 micg/p24/ml/2 10$^6$ cells/ml. Six days after in vitro stimulation, cytolytic capacity of cells was tested in a $^{51}$Cr test using des transduced HeLa-HDD target cells. Control target cells were HeLa-HDD cells transduced by the melanoma polyepitope (TRIP-mel-IRES-GFP). Results These experiments have been performed to study if HIV derived triplex positive vectors encoding a whole gene is capable of transducing cells and of inducing specific CTL responses against the target cells expressing the same gene. As illustrated in FIG. 9, specific lysis is obtained in all conditions. Transduced LPS-blast cells induced weak CTL responses. The best results were obtained using 1 micg/p24/ml of vector particles. These results show that an entire gene can be introduced in the genome of the host cell and its product is processed, presented and induce significant CTL responses. These results demonstrate also that des gene contains at least one or more HLA-A2.1 restricted CTL epitopic peptides.

REFERENCES

1. Naldini, L., Blomer, U., Gage, F. H., Trono, D. & Verma, I. M. Efficient transfer, integration, and sustained long-term expression of the transgene in adult rat brains injected with a lentviral vector. Proceedings of the National Academy of Sciences of the United States of America 93, 11382-8 (1996).
2. Naldini, L. Lentiviruses as gene transfer agents for delivery to non-dividing cells. Current Opinion in Biotechnology 9, 457-63 (1998).
3. Zufferey, R., Dull, T., Mandel, R. J., Bukovsky, A., Quiroz, D., Naldini, L. et al. Self-inactivating lentivirus vector for safe and efficient in vivo gene delivery. Journal of Virology 72, 9873-80 (1998).
4. Burns, J. C., Friedmann. T., Driever, W., Burrascano, M. & Yee, J. K. Vesicular stomatitis virus G glycoprotein pseudotyped retroviral vectors: concentration to very high titer and efficient gene transfer into mammalian and non-mammalian cells (see comments). Proceedings of the National Academy of Sciences of the United States of America 90, 8033-7 (1993).
5. Charneau P., Mirambeau, G., Roux, P., Paulous, S., Buc, H., & Clavel, F. HIV-1 reverse transcription. A termination step at the center of the genome. Journal of Molecular Biology 241, 651-62 (1994).
6. Pascolo, S., Bervas, N., Ure, J. M., Smith, A. G., Lemonnier, F. A. & Perarnau, B. HLA-A2.1-restricted education and cytolytic activity of CD8+ T lymphocytes from β2 microglobulin (β2m) HLA-A2.1 monochain transgenic H-2D$^b$ (β2m double knockout mice. J. Exp. Med. 185, 2043-2051 (1997).
7. Koenig, S., Gendelman, H. E., Orenstein, J. M., Dal Canto, M. C., Pezeshkpour, G. H., Yungbluth, M. et al. Detection of AIDS virus in macrophages in brain tissue from AIDS patients with encephalopathy. Science 233, 1089-93 (1986).
8. Roe, T., Reynolds, T. C., Yu, G. & Brown, P. O. Integration of murine leukemia virus DNA depend on mitosis. EMBO Journal 12, 2099-108 (1993).
9. Michel, M. L., Davis, H. L., Schleef, M., Mancini, M., Tiollais, P. & Whalen, R. G. DNA-mediated immunization to the hepatitis B Surface antigen in mice: aspects of the humoral response mimic hepatitis B viral infection in humans, Proceedings of the National Academy of Sciences of the United States of America 92, 5307-11 (1995).
10. Giovannangeli, C., Diviacco, S., Labrousse, V., Gryaznov, S., Charneau, P. & Helene, C Accessibility of nuclear DNA to triplex-forming oligonucleotides: the integrated provirus as a target. Proceedings of the National Academy of Sciences of the United States of America 94, 79-84 (1997).
11. Kim, V. N., Mitrophanous, K., Kingsman, S. M. & Kingsman, A. J. Minimal requirement for a lentivirus vector based on human immunodeficiency virus type 1. Journal of Virology 72, 811-6. (1998).
12. Fox, J. L. Researchers wary of fear-based ban on lentivirus gene therapy [news]. Nature Biotechnology 16, 407-8 (1998).
13. Dull, T., Zufferey, R., Kelly, M., Mandel., R. J., Nguyen, M., Trono, D. et al. A third-generation lentiviral vector with a conditional packaging system. Journal of Virology 72, 8463-71 (1998).
14. Arya, S. K., Zamani, M. & Kundra, P. Human immunodeficiency virus 2 lentivirus vectors for gene transfer: expression and potential for helper virus-free packaging. Human Gene Therapy 9, 1371-80 (1998).

The invention claimed is:

1. An isolated recombinant cell transduced by a replication-defective lentiviral vector comprising a transgene, a lentiviral cis-acting central initiation region (cPPT), and a lentiviral cis-acting termination region (CTS), such that a triplex DNA is formed during reverse transcription of the vector.

2. The recombinant cell of claim 1, wherein the lentiviral cPPT and CTS regions are HIV-1 cPPT and CTS regions.

3. The recombinant cell of claim 1, wherein the lentiviral cPPT and CTS regions are CAEV, EIAV, VISNA, HIV, SIV or FIV cPPT and CTS regions.

4. The recombinant cell of claim 1, wherein the lentiviral vector further comprises HIV-1 regulatory signals for reverse transcription and packaging.

5. The recombinant cell of claim 2, wherein the lentiviral vector further comprises HIV-1 regulatory signals for reverse transcription and packaging.

6. The recombinant cell of claim 1, wherein the cell is a non-dividing cell.

7. The recombinant cell of claim 2, wherein the cell is a non-dividing cell.

8. The recombinant cell of claim 3, wherein the cell is a non-dividing cell.

9. The recombinant cell of claim 4, wherein the cell is a non-dividing cell.

10. The recombinant cell of claim 5, wherein the cell is a non-dividing cell.

11. The recombinant cell of claim 1, wherein the cell is an antigen presenting cell.

12. The recombinant cell of claim 2, wherein the cell is an antigen presenting cell.

13. The recombinant cell of claim 3, wherein the cell is an antigen presenting cell.

14. The recombinant cell of claim 4, wherein the cell is an antigen presenting cell.

15. The recombinant cell of claim 5, wherein the cell is an antigen presenting cell.

16. The recombinant cell of claim 1, wherein the cell is a lung, brain, epithelial, astrocyte, mycroglia, oligodendrocyte, neuron, muscle, hepatic, dendritic, neuronal, bone marrow, macrophage, fibroblast, or hematopoietic cell.

17. The recombinant cell of claim 2, wherein the cell is a lung, brain, epithelial, astrocyte, mycroglia, oligodendrocyte, neuron, muscle, hepatic, dendritic, neuronal, bone marrow, macrophage, fibroblast, or hematopoietic cell.

18. The recombinant cell of claim 3, wherein the cell is a lung, brain, epithelial, astrocyte, mycroglia, oligodendrocyte, neuron, muscle, hepatic, dendritic, neuronal, bone marrow, macrophage, fibroblast, or hematopoietic cell.

19. The recombinant cell of claim 4, wherein the cell is a lung, brain, epithelial, astrocyte, mycroglia, oligodendrocyte, neuron, muscle, hepatic, dendritic, neuronal, bone marrow, macrophage, fibroblast, or hematopoietic cell.

20. The recombinant cell of claim 5, wherein the cell is a lung, brain, epithelial, astrocyte, mycroglia, oligodendrocyte, neuron, muscle, hepatic, dendritic, neuronal, bone marrow, macrophage, fibroblast, or hematopoietic cell.

21. The recombinant cell of claim 1, wherein the cell is a tumor or cancer cell.

22. The recombinant cell of claim 2, wherein the cell is a tumor or cancer cell.

23. The recombinant cell of claim 3, wherein the cell is a tumor or cancer cell.

24. The recombinant cell of claim 4, wherein the cell is a tumor or cancer cell.

25. The recombinant cell of claim 5, wherein the cell is a tumor or cancer cell.

* * * * *

SEQUENCE LISTING

<160> NUMBER OF SEQ ID NOS: 11

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(39)
<223> OTHER INFORMATION: Primer

<400> SEQUENCE: 1
tcagatctgc caccatggca ctaacagaag taataccac                              39

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(30)
<223> OTHER INFORMATION: Primer

<400> SEQUENCE: 2
cggaattctt attggccttg ccctgcttc                                         30

<210> SEQ ID NO 3
<211> LENGTH: 38
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(38)
<223> OTHER INFORMATION: Primer

<400> SEQUENCE: 3
gaagatctgc caccatgaag cccatcaacc tctctcat                               38

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(27)
<223> OTHER INFORMATION: Primer

<400> SEQUENCE: 4
cggaattctt acccagcgca acgcctc                                           27

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

```
<220> FEATURE:
<221> NAME/KEY: misc_feature
<222> LOCATION: (1)..(23)
<223> OTHER INFORMATION: Primer

<400> SEQUENCE: 5
ccggatcccc accggtcgcc acc                                          23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(23)
<223> OTHER INFORMATION: Primer

<400> SEQUENCE: 6
ccctcgagct agagtcgcgg ccg                                          23

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(38)
<223> OTHER INFORMATION: Triplex fragment

<400> SEQUENCE: 7
gtcgtcggcg ccgaattcac aaatggcagt attcatcc                          38

<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(34)
<223> OTHER INFORMATION: Triplex fragment

<400> SEQUENCE: 8
gtcgtcggcg ccccaaagtg gatctctgct gtcc                              34

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(32)
<223> OTHER INFORMATION: Primer

<400> SEQUENCE: 9
ccagatctac gcgtgccacc atggctgctg gt                                32

<210> SEQ ID NO 10
<211> LENGTH: 27
```

```
<212> TYPE: DNA
<213> ORGANISM: Artificial Sequence
<220> FEATURE:
<223> OTHER INFORMATION: Description of Artificial Sequence:
      oligonucleotide
<220> FEATURE:
<221> NAME/KEY: misc_feature
<222> LOCATION: (1)..(27)
<223> OTHER INFORMATION: Primer

<400> SEQUENCE: 10
cggaattcga cctaaacgca acggatg                                         27

<210> SEQ ID NO 11
<211> LENGTH: 92
<212> TYPE: PRT
<213> ORGANISM: human
<220> FEATURE:
<221> NAME/KEY: PEPTIDE
<222> LOCATION: (1)..(92)
<223> OTHER INFORMATION: melanoma epitope

<400> SEQUENCE: 11

Ala Ala Gly Ile Gly Ile Leu Thr Val Phe Leu Trp Gly Pro Arg Ala
  1               5                  10                  15

Leu Val Met Leu Leu Ala Val Leu Tyr Cys Leu Leu Leu Asp Gly Thr
             20                  25                  30

Ala Thr Leu Arg Leu Lys Thr Trp Gly Gln Tyr Trp Gln Val Tyr Met
         35                  40                  45

Asp Gly Thr Met Ser Gln Val Ile Thr Asp Gln Val Pro Phe Ser Val
     50                  55                  60

Tyr Leu Glu Pro Gly Pro Val Thr Ala Ile Leu Thr Val Ile Leu Gly
 65                  70                  75                  80

Val Leu Val Leu Pro Asp Val Phe Ile Arg Cys Val
                 85                  90
```